United States Patent
Kochte et al.

[11] Patent Number: 5,391,360
[45] Date of Patent: Feb. 21, 1995

[54] OVERCENTER, CAM DRIVEN LOCKING MECHANISM

[75] Inventors: Werner W. Kochte, Kent; Bill R. Stanford, Mentor, both of Ohio

[73] Assignee: Steris Corporation, Mentor, Ohio

[21] Appl. No.: 20,575

[22] Filed: Feb. 23, 1993

Related U.S. Application Data

[63] Continuation-in-part of Ser. No. 681,118, Apr. 5, 1991, Pat. No. 5,217,698, which is a continuation-in-part of Ser. No. 349,304, May 9, 1989, Pat. No. 5,091,343, which is a continuation-in-part of Ser. No. 140,388, Jan. 4, 1988, Pat. No. 4,892,706, which is a continuation-in-part of Ser. No. 826,730, Feb. 6, 1986, Pat. No. 4,731,222, said Ser. No. 681,118, is a continuation-in-part of Ser. No. 342,189, Apr. 24, 1989, Pat. No. 5,116,575, which is a continuation-in-part of Ser. No. 229,917, Aug. 8, 1988, Pat. No. 5,077,008, which is a continuation-in-part of Ser. No. 165,189, Mar. 7, 1988, Pat. No. 5,037,623, and a continuation-in-part of Ser. No. 140,388, Mar. 7, 1988, said Ser. No. 165,189, is a continuation-in-part of Ser. No. 826,730, Mar. 7, 1988, said Ser. No. 140,388, is a continuation-in-part of Ser. No. 826,730, Mar. 7, 1988.

[51] Int. Cl.⁶ .................................................. A61L 2/18
[52] U.S. Cl. ......................................... 422/292; 422/295; 422/297; 422/300; 292/11; 292/215; 292/229
[58] Field of Search .................... 134/57 DL, 58 DL; 292/11, 46, 100, 215, 216, 229; 422/292, 295, 297, 300; 435/31, 311, 809

[56] References Cited

U.S. PATENT DOCUMENTS

| | | | |
|---|---|---|---|
| 199,265 | 1/1878 | Cogswell | 292/215 |
| 1,658,686 | 2/1928 | Mory | 292/100 |
| 2,841,430 | 7/1958 | Krause | 292/11 |
| 2,996,324 | 8/1961 | Krause | 292/11 X |
| 3,133,168 | 5/1964 | Jacobson | 134/58 DL X |
| 3,240,523 | 3/1966 | Heimann | 292/229 X |
| 3,287,049 | 11/1966 | Shay | 292/229 |
| 3,601,434 | 8/1971 | Fargo et al. | 292/46 |
| 3,857,002 | 12/1974 | Lay et al. | 200/61.64 |
| 3,985,023 | 10/1976 | Grath | 70/267 |
| 4,086,938 | 5/1978 | Churley | 137/586 |
| 4,703,961 | 11/1987 | Weinerman et al. | 292/216 |
| 4,773,693 | 9/1988 | Premji et al. | 296/65.1 |
| 5,091,343 | 2/1992 | Schneider et al. | 422/297 |
| 5,217,698 | 6/1993 | Siegel et al. | 422/295 |

FOREIGN PATENT DOCUMENTS

| | | |
|---|---|---|
| 0559772 | 9/1923 | France . |
| 0778438 | 9/1933 | France . |
| 0154466 | 7/1932 | Switzerland . |

OTHER PUBLICATIONS

One page drawing from German patent Nr. 208,620.
Steris Advertising Brochure "Sterile Processing ... Just in Time", 1992.

Primary Examiner—James C. Housel
Assistant Examiner—Harold Y. Pyon
Attorney, Agent, or Firm—Fay, Sharpe, Beall, Fagan, Minnich & McKee

[57] ABSTRACT

A microbial decontamination unit (A) has a door (B) which is hingedly mounted (90) to the housing. When the door is opened, the operator has access to a decontamination chamber (22), a mixing chamber (10) for receiving an anti-microbial solution concentrate, and other anti-microbial solution circulation paths (18). A mechanical locking mechanism (D) selectively locks the door member against a gasket (92) to assure that the anti-microbial solution does not leak between the door and the housing. The latch mechanism includes a hook member (54) that defines a circular bearing surface (52) that is rotatably received on a circular cam member (50). The circular cam member (50) is eccentrically mounted on a shaft (40). Rotation of the shaft and cam member moves a latch engaging surface (56) of the hook member into and out of engagement with a latch member (58) along an axis of travel (76). The cam member is selectively rotated a few degrees (78) past the axis of travel to provide an overcenter locking arrangement (FIG. 9C). To open the door, the shaft is rotated the opposite direction first lifting the latch engaging surface off the latch member and then rotating an accelerator member (84) into the hook member. Continued rotation causes the accelerator member to rotate the hook member around the circular bearing (50) against the resilient bias force of a spring (70) (FIG. 9A).

17 Claims, 7 Drawing Sheets

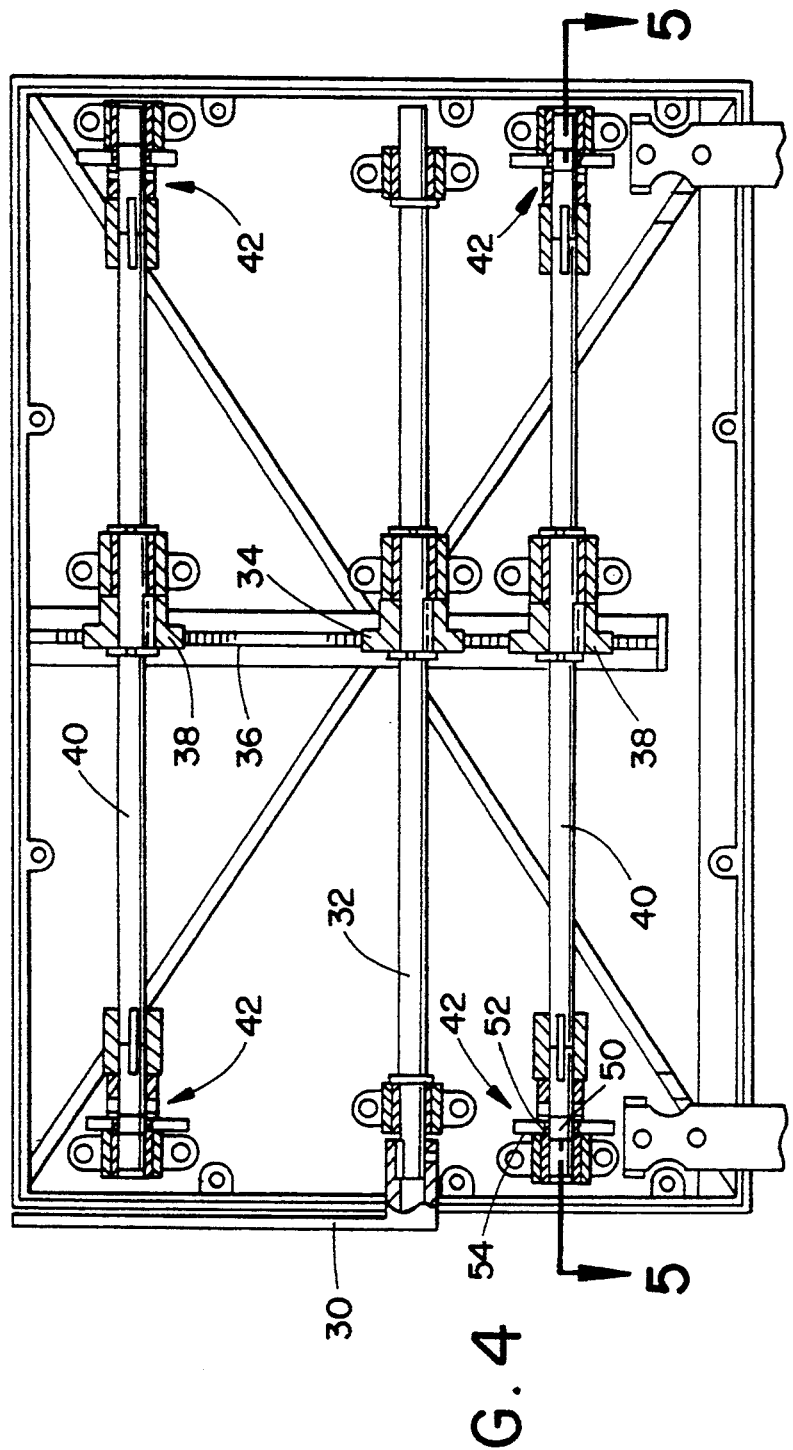
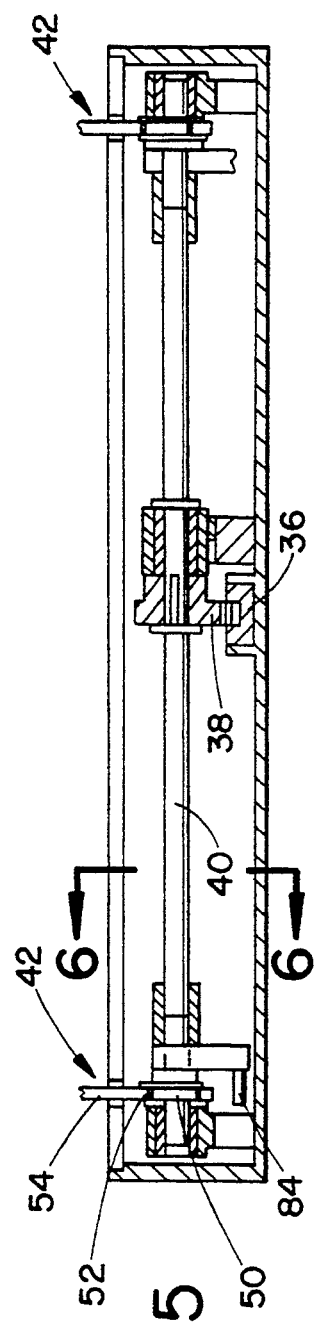
FIG. 4
FIG. 5

OVERCENTER, CAM DRIVEN LOCKING MECHANISM

This application is a continuation-in-part of U.S. application Ser. No. 07/681,118, filed Apr. 5, 1991, now U.S. Pat. No. 5,217,698, which, in turn, is a continuation-in-part of U.S. application Ser. No. 07/349,304, filed May 9, 1989, now U.S. Pat. No. 5,091,343, which, in turn, is a continuation-in-part of U.S. application Ser. No. 07/140,388, filed Jan. 4, 1988, now U.S. Pat. No. 4,892,706, which, in turn, is a continuation-in-part of U.S. application Ser. No. 06/826,730, filed Feb. 6, 1986, now U.S. Pat. No. 4,731,222, said U.S. application Ser. No. 07/681,118, is also a continuation-in-part of U.S. application Ser. No. 07/342,189, filed Apr. 24, 1989, now U.S. Pat. No. 5,116,575, which, in turn, is a continuation-in-part of U.S. application Ser. No. 07/229,917, filed Aug. 8, 1988, now U.S. Pat. No. 5,077,008, which, in turn, is a continuation-in-part of U.S. application Ser. No. 07/165,189, filed Mar. 7, 1988, now U.S. Pat. No. 5,037,623, and also a continuation in part of U.S. application Ser. No. 07/140,388, now U.S. Pat. No. 4,892,706, which are also continuations-in-part of U.S. application Ser. No. 06/826,730, now U.S. Pat. No. 4,731,222.

BACKGROUND OF THE INVENTION

The present invention pertains to the latch and locking art. It finds particular application in conjunction with latching a door to medical sterilizing equipment with sufficient force that a fluid tight seal is created. It is to be appreciated, however, that the present latching mechanism will also find application in locking or sealing doors to retain other fluids, in deep sea applications, in space applications, in sealing against hazardous vapor and fluid contamination, and in other applications in which a very high sealing force is advantageous. Moreover, the present invention also has security application in which doors, windows, and other movable elements are to be locked and resist tampering.

Prior U.S. patent application Ser. No. 07/681,118 describes a sterilizing apparatus in which an access door is vacuum sealed in a closed position during operation. That is, the door opens to allow access to a sterilization chamber, a sterilant mixing chamber, and various liquid sterilant flow paths. After the equipment to be sterilized is loaded into the sterilizing chamber and a dose of sterilant concentrate is loaded into the mixing chamber, the door is closed. The door is held closed by drawing a vacuum between a pair of circumferential gaskets around the periphery of the door.

Although the vacuum seal created a secure fluid tight seal under normal operating conditions, it is considered undesirable to have fluid leakage even under abnormal operating conditions. For example, dropping a heavy object on the door or banging the door with a cabinet door or elbow could jar the sterilizer door sufficiently to allow a momentary fluid leakage. Moreover, with age, the rubber gaskets would tend to seal less well, reducing the vacuum seal and, hence, the reliability.

Various mechanical hooking mechanisms are known in the art. For example, rigid, pivoted hooks have been used which slidingly engage and cam a latch pin. However, such rigid, pivoted hooks tend to require a relatively high latching pressure. Further, the camming action causes wear on the latch pin, allowing the latching to become sloppy or loose with repeated use. Multipiece latches with an internal gear arrangement have been successful in obtaining a relatively high holding force with a relatively small closing force. However, the mechanical linkages tended to be complex, difficult to adjust, and subject to damage or deformation.

In accordance with the present invention, a new and improved latching mechanism is provided which achieves a very high holding force with a very small closing force.

SUMMARY OF THE INVENTION

In accordance with one aspect of the present invention, a microbial decontamination apparatus is provided. The apparatus includes a main housing and a door or closure. A microbial decontamination chamber and fluid sterilant flow paths are provided to which access is provided by opening the door or closure. A means is provided for circulating an anti-microbial fluid through the passages and the decontamination chamber. A mechanical locking means selectively locks the door or closure to the housing.

In accordance with another aspect of the present invention, a mechanical locking mechanism is provided which may be used either with the microbial decontamination apparatus or others. The locking mechanism includes a rotatable shaft means to which an eccentric or cam surface is connected. A hook member is rotatably mounted on the cam or eccentric surface such that as the shaft is rotated, the hook member is displaced toward and away from a latch pin or surface.

In accordance with a more limited aspect of the present invention, a biasing means is provided for biasing the hook member toward the latch pin or surface such that rotation of the shaft causes the hook member to move along a path which is substantially orthogonal to the latch pin or surface.

In accordance with another more limited aspect of the present invention, an accelerator pin or surface means is connected with the shaft for rotation therewith. The accelerator surface is oriented relative to the cam surface such that after the hook member disengages the latch pin or surface, the accelerator surface engages the hook member and urges the hook member against the biasing means in a direction generally orthogonal to the direction of travel and away from the latch pin.

In accordance with another more limited aspect of the present invention, the cam member rotates overcenter. More specifically, after the hook member has engaged the latch pin or surface, the cam member rotates another few degrees. Although movement past center tends to reduce the force on the latch surface slightly, the hook and latch surface can only be disengaged by rotating the cam though the increased pressure center region.

One advantage of the present invention is that the door or closure element is securely and assuredly latched.

Another advantage of the present invention is that relatively small closing forces achieve a relatively high holding force.

Another advantage of the present invention resides in its simplicity and reliability even with repeated use.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 4 is a plan view of the interior of the door member with its outer or cosmetic cover removed;

FIG. 5 is a sectional view through section 5—5 of FIG. 4;

DETAILED DESCRIPTION OF THE PREFERRED EMBODIMENT

With reference to FIGS. 1-4, a microbial decontamination apparatus, e.g. a sterilizing or disinfecting apparatus A, is configured to sit on a countertop or other convenient work surface. A front door B is manually openable to provide access to a microbial decontamination region C. A locking or latching mechanism D selectively locks the door or closure member B securely against the main housing portion of the microbial decontaminating apparatus A.

Figure 1:
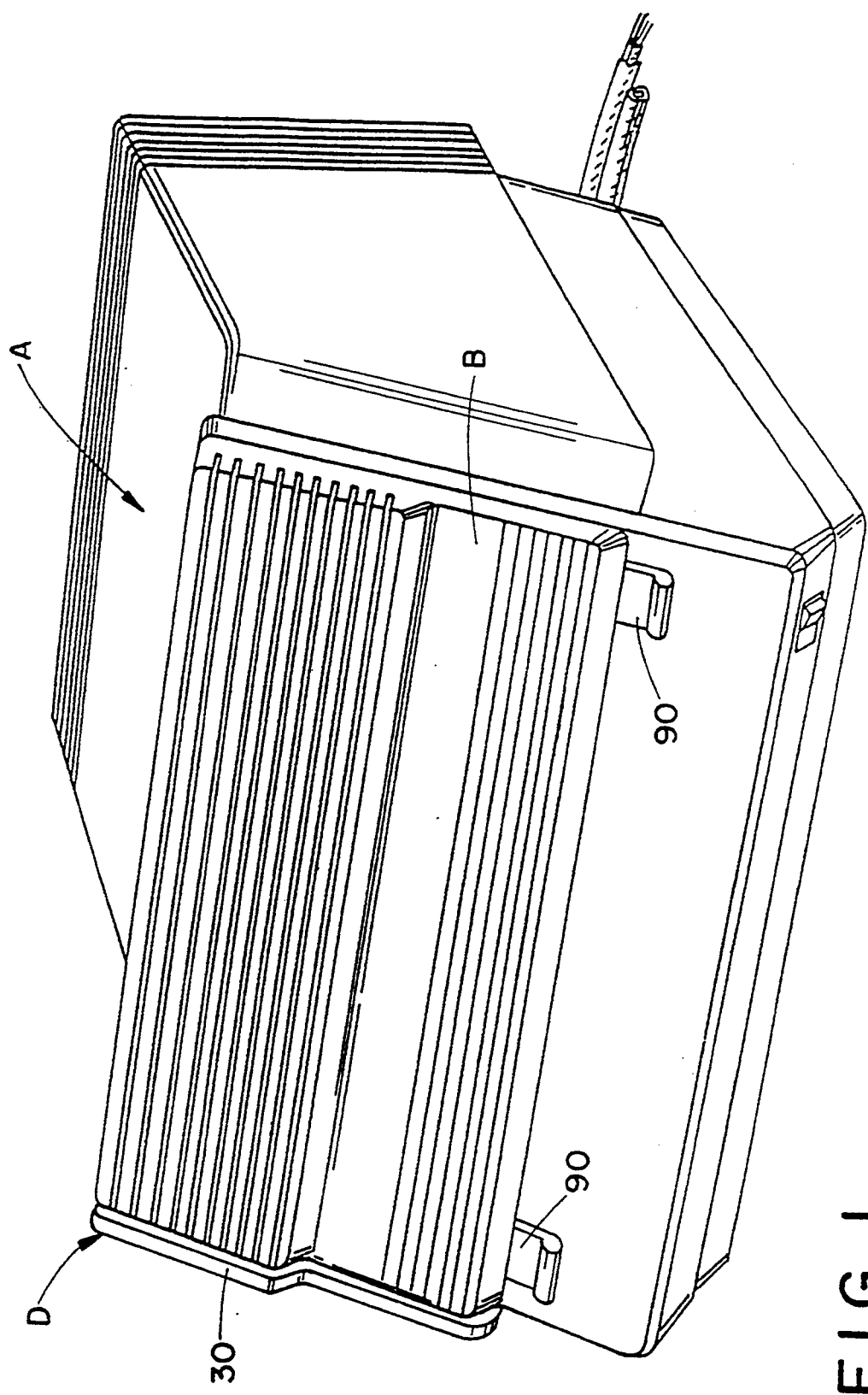
FIG. 1 is a perspective view of a liquid microbial decontamination apparatus in accordance with the present invention.
Figure 2:
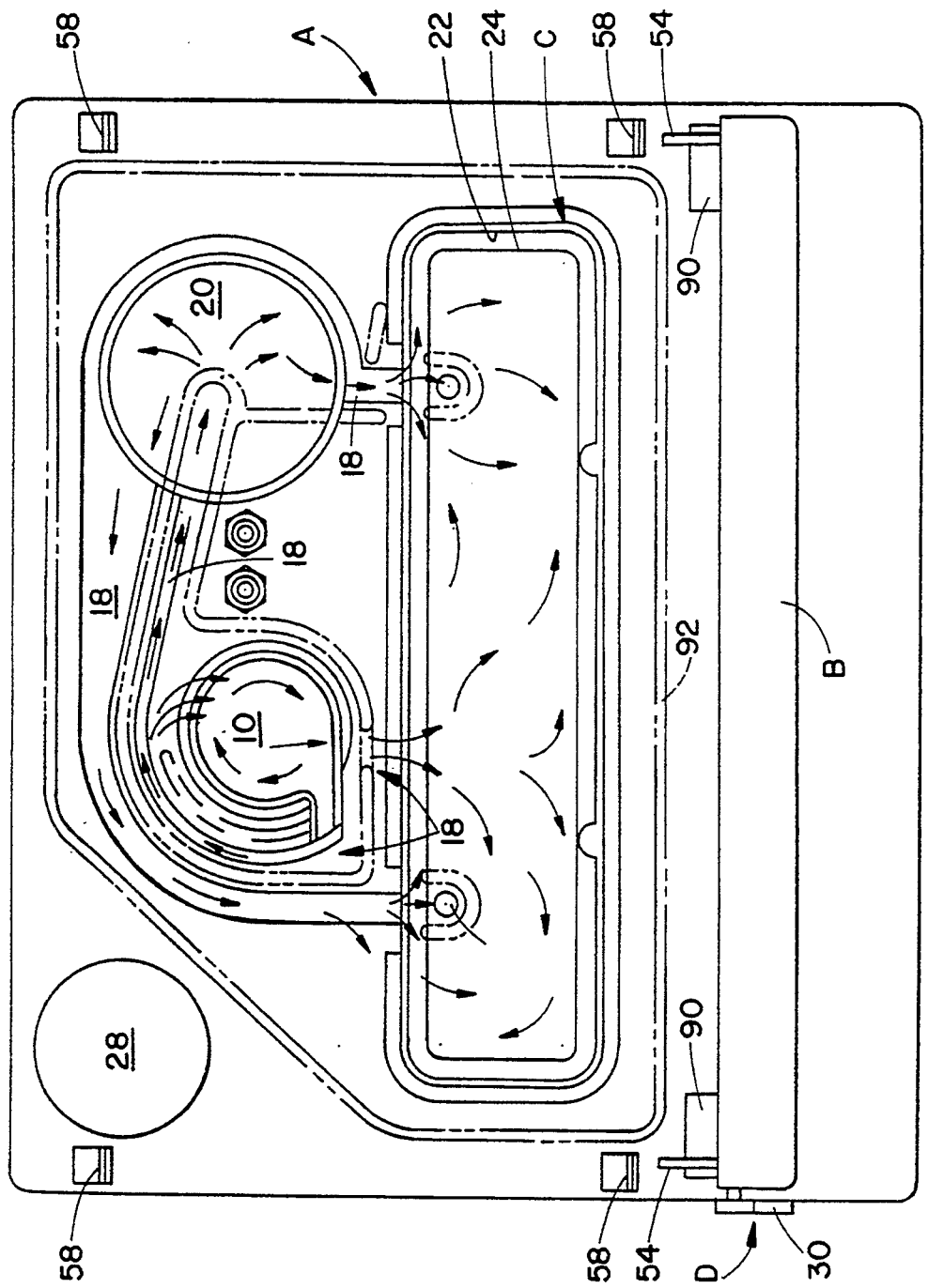
FIG. 2 is a front view of the system of FIG. 1 with the door open.
Figure 3:
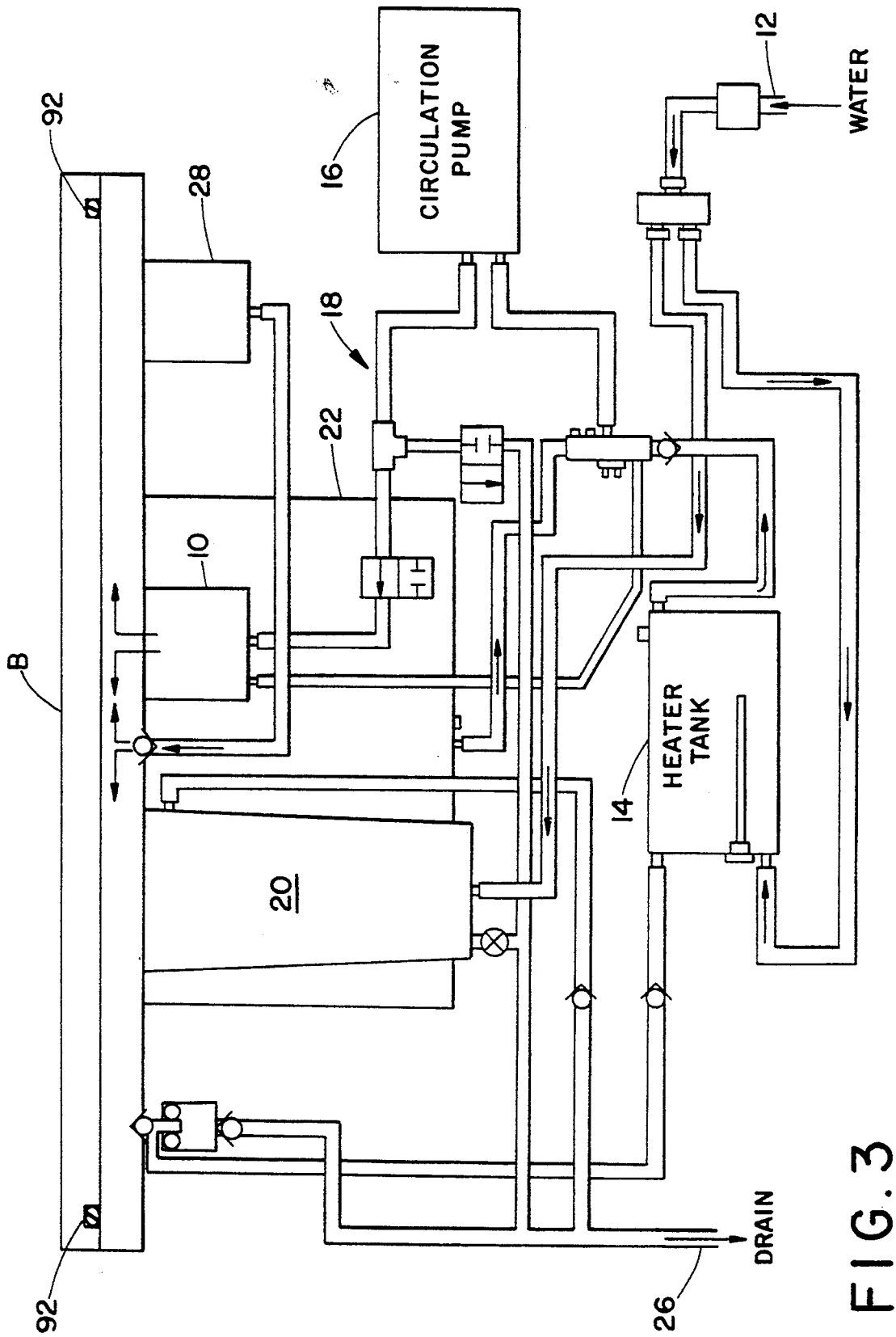
FIG. 3 is a plumbing diagram of the anti-microbial solution carrying paths of the microbial decontamination apparatus of FIG. 1.

With particular reference to FIGS. 2 and 3, the microbial decontamination region C includes a sterilant or other microbial decontamination solution mixing region The mixing region 10 receives a premeasured dose of a microbial decontaminant concentrate, preferably in powdered form. Water from an inlet 12 is selectively heated in a heater tank 14 and circulated by a circulation pump 16 to the mixing chamber 10 to form a sterilant or other anti-microbial solution.

Although various anti-microbial agents may be utilized, in the preferred embodiment, the anti-microbial concentrate is a mixture of powders which react when wet to form a sterilant, such as a strong oxidant, corrosion inhibitors, and a wetting agent. More specifically to the preferred embodiment, the dry ingredients include a water soluble acid precursor and a water soluble persalt which, when dissolved in water, forth an acid solution with an anti-microbially effective concentration. The dry ingredients further include a buffer, e.g. a borate, for bringing the pH to a neutral level to inhibit steel corrosion. The dry ingredients include other corrosion inhibitors, such as a molybdate for inhibiting steel corrosion, a triazole for inhibiting copper and brass corrosion, and the like. Powdered sequestering agents may be included for inhibiting harmful precipitation in hard water. In the preferred embodiment, the acid precursor is acetylsalicylic acid and the persalt is sodium perborate, present in sufficient quantity that the resultant solution has at least a 0.2% w/v concentration of peracetic acid.

Other anti-microbial agents can also be generated in situ, such as chlorine dioxide, chlorine, hydrogen peroxide, and mixtures thereof. The powdered corrosion inhibitors may further include a mixture of potassium chromates, sodium chloride, arid phosphates. Other copper and brass corrosion inhibitors include benzotriazoles, tolytriazoles, mercaptobenzathiazole, azoles, benzoates, and other five ring compounds. Other steel anti-corrosives include chromates, dichromates, tungsdates, vanidates, borates, and combinations thereof.

After the circulation pump 16 circulates the heated water through the mixing chamber 10, the anti-microbial solution flows through a series of passageways 18 defined by the outer face of the housing A or the inner face of the door B. The passageways carry the anti-microbial solution over an inner surface of a rinse fluid filter 20 and into a sterilizing or decontamination chamber 22. Preferably, a cassette 24 is slidably receivable in the decontamination chamber 22 to carry the items to be decontaminated. The anti-microbial solution is circulated through the flow passages such that every surface from the rinse water filter 20 downstream through the passages 18 and the decontamination chamber 22 are microbially decontaminated, preferably sterilized. After a preselected duration, the solution is drained 26 and rinse water is introduced. The rinse water flows into the filter 20 which filters all harmful microbes from the incoming water, i.e. disinfects the rinse water. The circulation pump 16 circulates the microbially decontaminated rinse water through the paths 18, the decontamination chamber 22, and the cassette 24. In order to prevent contamination from airborne microbes, an air microbe decontamination filter 28 filters air which is drawn into the system to replace the drained rinse and anti-microbial solutions.

With reference to FIGS. 4-8, the latch means D includes a user operated handle 30 which rotates between locked and open positions. As the handle rotates, it rotates a first shaft 32. Shaft 32 rotates a cam or gear member 34 whose teeth engage a rack gear 36. The rack gear 36 engages a pair of driven gear members The driven gear members are each connected with a driven shaft 40. In this manner, the gears 34-38 function as a mechanical motion, particularly a rotation, transfer means. It is contemplated that other means may be provided for transferring the rotation of the first or control shaft 32 with the driven shafts 40. Each of the driven shafts drive a hook assembly 42.

Each of the hook assemblies includes a cam member 50 which is mounted eccentrically to shaft 40 for rotation therewith. The circular cam member is rotatably received in a circular bearing or journal member 52 which is connected with a hook member 54. In this manner, the hook member is mounted in a freely rotational relationship with the cam member 50, hence the driven shaft 40. The hook member has a latch pin engaging surface 56 which selectively engages a latch pin 58 or other latch surface located on the body portion A.

Figure 7:
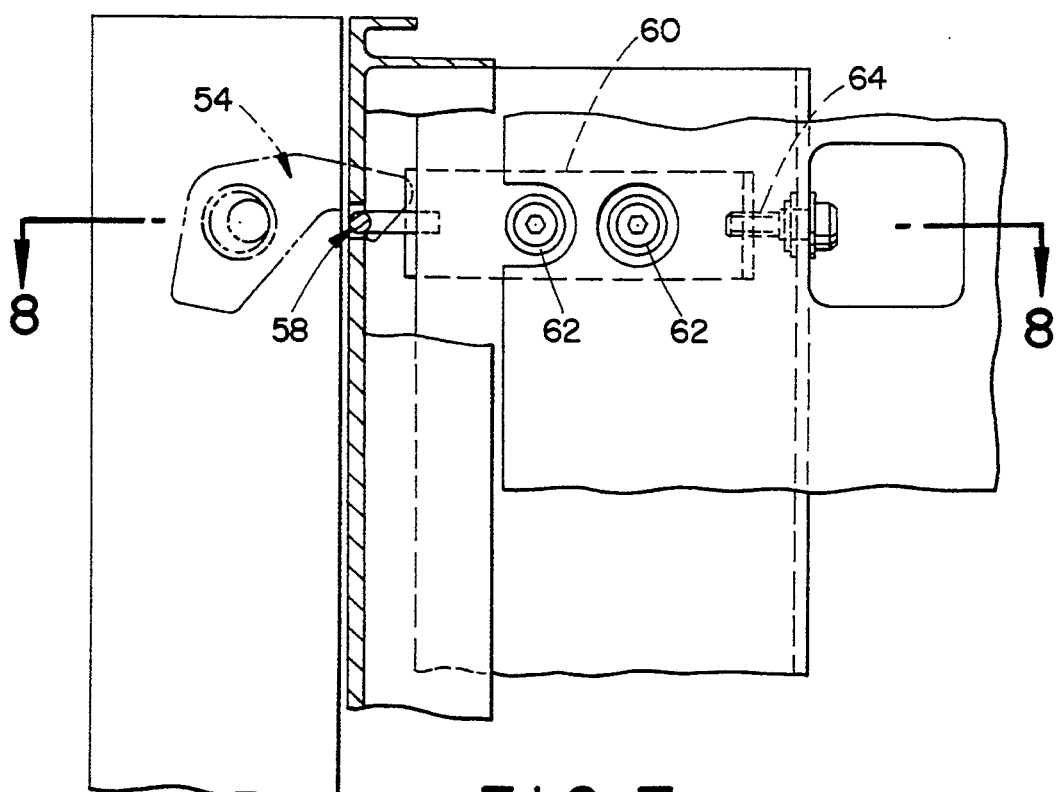
FIG. 7 is a detailed view analogous to FIG. 6, but showing the latching pin and latching pin adjustment mechanisms.
Figure 8:
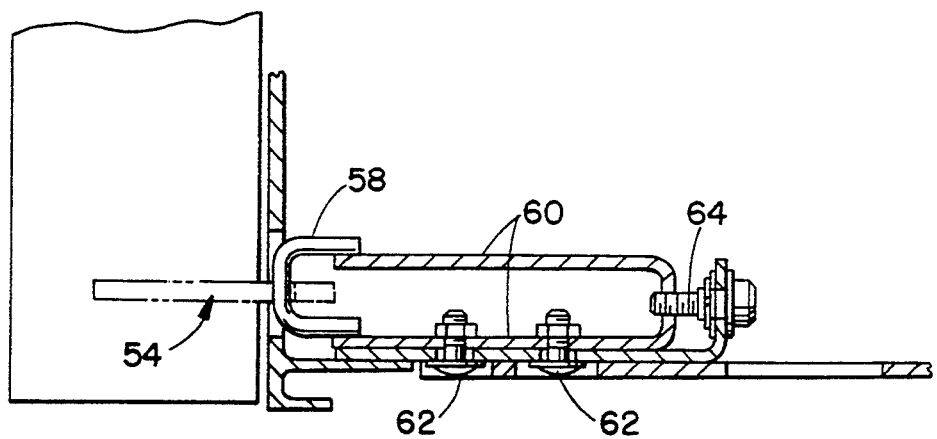
FIG. 8 is a view along section 8—8 of FIG. 7.

With particular reference to FIGS. 7 and 8, the latch pin 58 is mounted to a carrier 60 which is slidably received in mounting bolts 62. A threaded member 64 selectively slides the carriage 60 to adjust the exact position of the latch pin or surface 58 relative to the latch engaging surface 56. Once the latch pin is suitably positioned, members 62 are tightened to clamp the carriage 60 against further motion.

Figure 6:
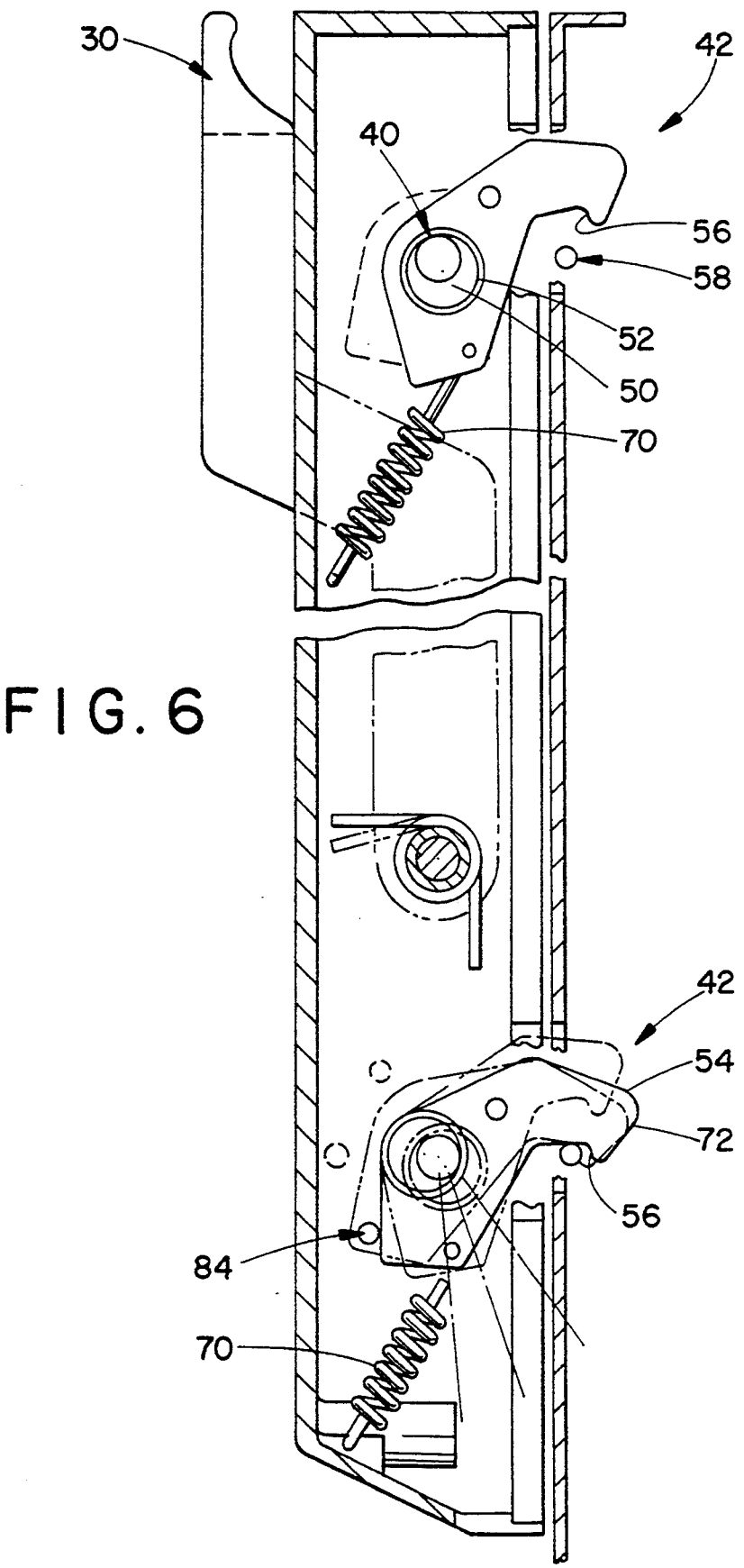
FIG. 6 is a sectional view along section 6—6 of FIG. 4.
Figure 9A:
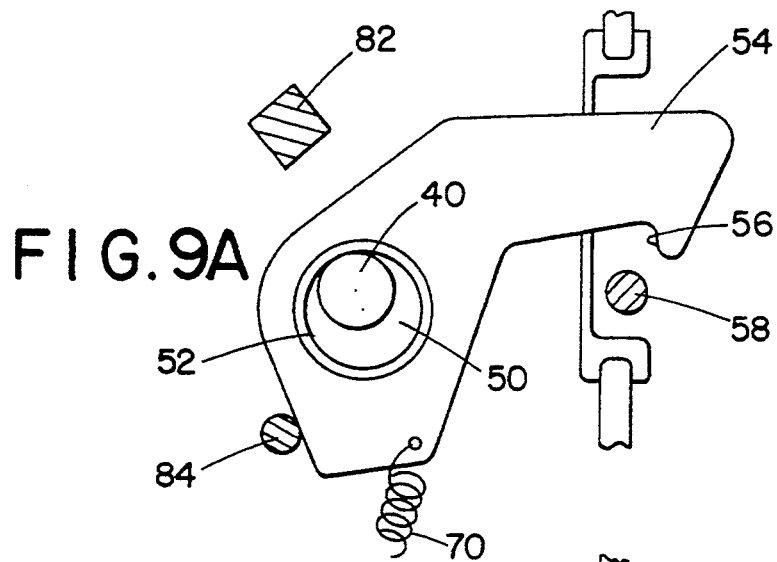
FIGS. 9A, 9B, and 9C illustrate movement of the hook from a totally open position in FIG. 9A, through a neutral position in FIG. 9B, to a final closed position in FIG. 9C.
Figure 9B:
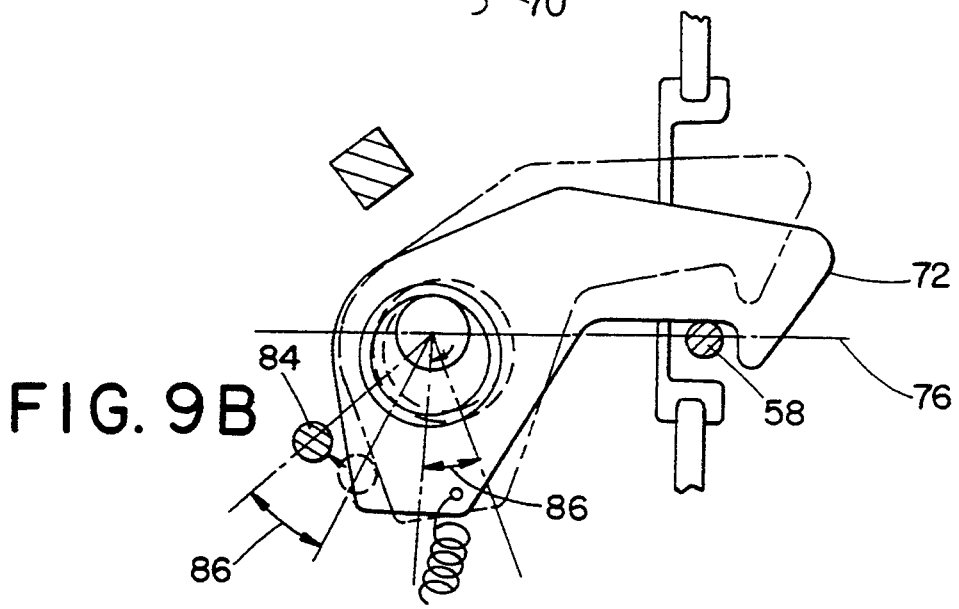

With particular reference to the lower latch on FIG. 6 and FIG. 9B, a spring or other biasing means 70 biases the hook member to a neutral position in which it abuts the latch pin 58 with the latch pin engaging surface 56 displaced in a direction of travel. The latch hook 54 has a cam surface 72 such that when the door is closed from the open position to the closed position, the interaction between the cam surface 72 and the latch pin 58 biases the hook against the spring member 70 to allow the door to close. To latch the door, the operator rotates the handle 30, rotating shaft 40 such that the highest point of the cam 50 moves from direction 74 into alignment with the direction of travel 76 through the latch pin 58 and the shaft 40 and beyond a few degrees 78 to a latched or locked position 80. In this manner, the cam is rotated overcenter by angle 78, preferably about 5 degrees. A stop, such as stop 82 engages an element which rotates with shaft 40 to prevent further rotation in the latching direction.

Figure 9C:
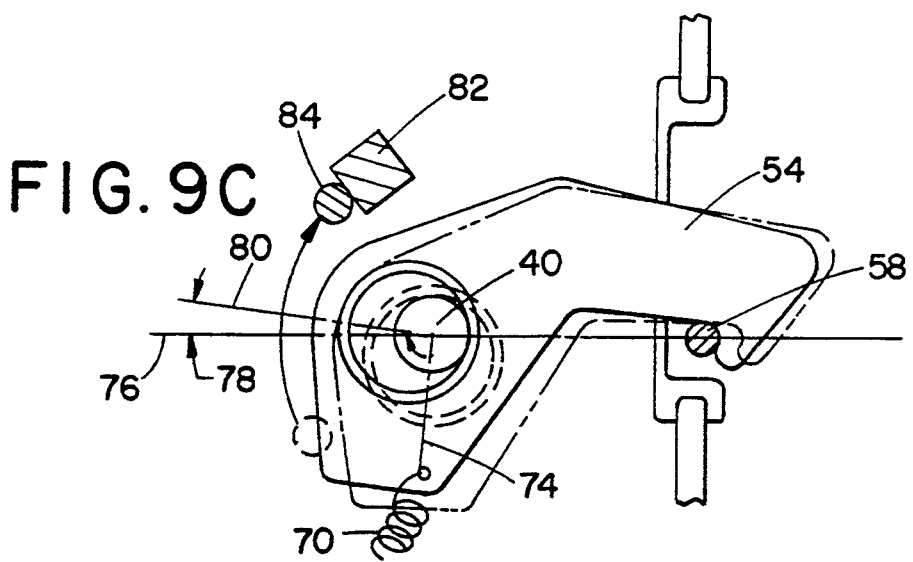

The mechanical linkage means 34–38 may have a 1:1 gear ratio or may have a gear ratio which causes the operator to move the handle further, but with a lower force to achieve the locking configuration of FIG. 9C. Once the hook member is locked, unlocking requires moving the major axis of the cam member 50 across the center axis 76. Thus, in order to release the hook, the hook must first be locked yet more tightly against the latch pin 58.

To release the latching means, the driven shaft 40 is rotated in the opposite direction to return the high point of the cam to direction 74. It should be noted that the driven shaft 40 and the cam 50 are rotating to the hook member 54 which shifts generally along axis 76. In order to move the hook member out of alignment with the latch pin 58, an accelerator pin or surface 84 is mounted to the shaft 40 for rotation therewith. The accelerator pin is mounted on the shaft 40 at an appropriate angle that it does not engage the hook member 54 in the neutral position of FIG. 9B or the latched position of FIG. 9C. However, a small additional rotation by an angle 86 in the unlocking direction, moves the accelerator pin 84 into contact with the hook member and rotates the hook member to the open position as illustrated in FIG. 9A. After the door is opened and the operator releases the handle 30, the spring or biasing means 70 urges the hook member back the neutral position of FIG. 9B.

The door is mounted to the body by hinges 90. The hinges 90, are preferably relatively loose in the sense that the hinges do not assist in locking the door B tightly against a sealing gasket 92. Rather, the hinges allow the door to undergo limited movement relative to the gasket 92. The four or more locking latching assemblies 42 supply the locking force between the door and the housing. Although illustrated with the locking mechanism in the door and the latch pins in the body, it is to be appreciated that the latch pins can be mounted in the door and the locking assembly and handle on the body.

Although the locking assembly is illustrated in conjunction with a microbial decontamination device, it is to be stressed that the locking assembly can be used to lock any two elements together. For example, note that the high latching force effectively prevents disengagement without the lever arm of the handle. If the handle is removed, a security locking system is provided.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A microbial decontamination system comprising:
   a housing portion including a microbial decontamination chamber for receiving items to be microbially decontaminated and a microbial solution circulating means for selectively circulating a microbial decontamination fluid through the microbial decontamination chamber;
   a door member connected with the housing portion for movement about a generally vertical access between an open and a closed position, the door member providing access to the microbial decontamination chamber in the open position and providing a fluid tight seal in the closed position;
   a mechanical locking means for mechanically locking the door member into an assured fluid tight sealing relationship with the housing portion, the mechanical locking means including:
      a latch surface mounted to one of the housing portion and the door member;
      a circular cam member eccentrically mounted relative to an axis of rotation;
      a hook member having a latch engaging surface, the hook member being rotatably mounted on the cam member such that the hook member and the cam member are free to undergo relative rotation, the cam member moving the latch engaging surface of the hook member generally along an axis of travel which extends through the axis of rotation and the latch surface to move the hook member between at least a latch surface engaging, locked position and a latched surface disengaged, unlocked position;
      a rotating means for rotating the cam member about the axis of rotation to move the hook member at least between the locked and unlocked positions, the rotating means rotating a major axis of the cam a few degrees past the axis of travel in an overcenter locking movement; and
      a stop means for preventing the rotating means from rotating the cam member beyond the few degrees past the axis of travel.

2. The system as set forth in claim 1 wherein the circulating means is connected with a source of water and the housing further defines an antimicrobial concentrate receiving region that is accessible through the door to receive a premeasured does of an antimicrobial concentrate, the antimicrobial concentrate receiving chamber being connected with the circulating means to have water circulated therethrough to form an antimicrobial solution for circulation through the microbial decontamination chamber.

3. A microbial decontamination system comprising:
   a housing portion including a microbial decontamination chamber for receiving items to be microbially decontaminated and a microbial solution circulating means for selectively circulating a microbial decontamination fluid through microbial decontamination chamber;

a door member connected with the housing portion for movement between an open and closed position, the door member providing access to the microbial decontamination chamber in the open position and providing a fluid tight seal in the closed position;

a mechanical locking means for mechanically locking the door member into an assured fluid tight sealing relationship with the housing portion, the mechanical locking means including:

a latch surface mounted to one of the housing portion and the door member;

a cam member having an arcuate surface portion;

a hook member having a latch engaging surface, the hook member being rotatably mounted on the cam member arcuate surface portion such that the hook member and the cam member are free to undergo rotation relative to each other, the hook member being moveable between at least a latch surface engaging, locked position and a latched surface disengaged, unlocked position;

a rotating means for rotating the cam member arcuate surface portion overcenter to move the hook member at least between the locked and unlocked positions, into and out of engagement with the latch surface.

4. The system as set forth in claim 3 wherein the cam member is eccentrically mounted relative to an axis of rotation, the cam member moving the latch engaging surface of the hook member generally along an axis of travel which extends through the axis of rotation and the latch surface, the rotating means rotating a major axis of the cam a few degrees past the axis of travel in an overcenter locking movement, and further including a stop means for preventing the rotating means from rotating the cam member beyond the few degrees past the axis of travel.

5. The system as set forth in claim 4 wherein the latch surface is defined on a generally U-shaped member which is adjustable along the axis of travel.

6. The system as set forth in claim 3 further including a resilient biasing means for biasing the hook member toward the latch surface.

7. The system as set forth in claim 6 further including an accelerator member which is rotated concurrently with the cam member to engage the hook member after the hook member latch engaging surface is moved out of engagement with the latch surface to cause the hook member to rotate about the cam member against the biasing force of the resilient biasing means.

8. The system as set forth in claim 3 wherein the rotating means includes a shaft and the cam means includes a circular cam member which is eccentrically mounted relative to the shaft, the hook member defining a circular bearing surface which rotatably receives the circular cam surface therein.

9. A microbial decontamination system comprising:

a housing portion including a microbial decontamination chamber for receiving items to be microbially decontaminated and a microbial solution circulating means for selectively circulating a microbial decontamination fluid through the microbial decontamination chamber;

a door member connected with the housing portion for movement between an open and a closed position, the door member providing access to the microbial decontamination chamber in the open position and providing a fluid tight seal in the closed position;

a mechanical locking means for mechanically locking the door member into an assured fluid tight sealing relationship with the housing portion, the mechanical locking means including a latch surface mounted to one of the door member and the housing portion;

a hook member having a latch engaging surface, the hook member being rotatably mounted on a cam member such that the hook member and the cam member are free to rotate relative to each other;

a rotating means for rotating the cam member to move the hook member into and out of engagement with the latch surface; and an accelerator member which is rotated concurrently with the cam member and engages the hook member after the hook member latch engaging surface is moved out of engagement with the latch surface to cause the hook member to rotate about the cam member out of alignment with the latch surface.

10. The system as set forth in claim 9 wherein the cam member is eccentrically mounted relative to an axis of rotation, the cam member moving a latch engaging surface of the hook member generally along an axis of travel which extends through the axis of rotation and the latch surface, the rotating means rotating a major axis of the cam a few degrees past the axis of travel in an overcenter locking movement, and further including a stop means for preventing the rotating means from rotating the cam member beyond the few degrees past the axis of travel.

11. The system as set forth in claim 9 further including a resilient biasing means for biasing the hook member toward the latch surface.

12. The system as set forth in claim 9 wherein the rotating means includes a shaft and the cam means includes a circular cam member which is eccentrically mounted relative to the shaft, the hook member defining a circular bearing surface which rotatably receives the circular cam surface therein.

13. The system as set forth in claim 9 wherein the latch surface is defined on a generally U-shaped member and further including a means for adjustably positioning the U-shaped member.

14. A fluid microbial decontamination system comprising:

a housing portion including a chamber for receiving items to be microbially decontaminated and a means for circulating a microorganism killing fluid through the chamber to kill at least pathogenic microorganisms on the items;

a door connected with the housing portion, the door being movable between an open position for providing access to the chamber and a closed position in which it provides a fluid-tight seal;

an overcenter, cam driven locking means for locking the door in the closed position, the overcenter, cam driven locking means including:

a shaft rotatably mounted to one of the door and the housing portion;

a means for selectively rotating the shaft;

a cam member having a cam surface extending along at least a circular arc segment, the cam member being mounted to the shaft for rotation therewith, the cam member being mounted such that the cam surface extends eccentrically to the shaft;

a hook member having a bearing surface within which the cam surface is rotatably received, the hook member having a latch engaging surface which is caused by rotation of the shaft and cam member to move generally along an axis of travel into and out of engagement with a latch mounted to the other of the door and the housing portion, the axis of travel extending through the shaft and the latch.

15. The fluid microbial decontamination system as set forth in claim 14 further including a stop means for limiting rotation of the cam member such that a major axis of the cam member rotates through the axis of travel and is constrained by the stop means from rotating beyond a few degrees past the axis of travel, whereby an overcenter latching motion is provided.

16. The fluid microbial decontamination system as set forth in claim 14 further including:

an accelerator member which is connected to the shaft for rotation therewith, the accelerator member being rotated into engagement with the hook member by continued rotation of the shaft after the hook member latch engaging surface disengages the latch, the acceleration member causing the hook member to rotate about the cam member such that the latch engaging surface rotates away from the latch.

17. The fluid microbial decontamination system as set forth in claim 16 further including a biasing means for biasing the latch engaging surface of the hook member toward the latch.

* * * * *